US012029485B2

(12) United States Patent
Fukuma et al.

(10) Patent No.: US 12,029,485 B2
(45) Date of Patent: Jul. 9, 2024

(54) OPHTHALMIC MICROSCOPE

(71) Applicant: Topcon Corporation, Tokyo (JP)

(72) Inventors: Yasufumi Fukuma, Tokyo (JP);
Kazuhiro Oomori, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 1147 days.

(21) Appl. No.: 16/642,052

(22) PCT Filed: Aug. 28, 2018

(86) PCT No.: PCT/JP2018/031844
§ 371 (c)(1),
(2) Date: Nov. 20, 2020

(87) PCT Pub. No.: WO2019/044861
PCT Pub. Date: Mar. 7, 2019

(65) Prior Publication Data
US 2021/0068654 A1    Mar. 11, 2021

(30) Foreign Application Priority Data

Aug. 30, 2017 (JP) ................ 2017-165187
Aug. 31, 2017 (JP) ................ 2017-167793
May 8, 2018  (JP) ................ 2018-090269

(51) Int. Cl.
*A61B 3/117*    (2006.01)
*A61B 3/10*     (2006.01)
*A61B 3/13*     (2006.01)

(52) U.S. Cl.
CPC ............. *A61B 3/117* (2013.01); *A61B 3/102* (2013.01); *A61B 3/132* (2013.01)

(58) Field of Classification Search
CPC .......... A61B 3/117; A61B 3/102; A61B 3/132
(Continued)

(56) References Cited

U.S. PATENT DOCUMENTS

2012/0092615 A1* 4/2012 Izatt ............... A61B 3/102
                                                    351/205
2018/0116502 A1* 5/2018 Ishinabe ......... A61B 3/117
2020/0214555 A1* 7/2020 Fukuma ......... A61B 3/102

FOREIGN PATENT DOCUMENTS

JP    2017023584 A  *  2/2017
JP    2017023584 A     2/2017
JP    2018110785 A     7/2018

OTHER PUBLICATIONS

International Search Report and Written Opinion issued in PCT/JP2018/031844, dated Nov. 20, 2018.
(Continued)

*Primary Examiner* — Sharrief I Broome
(74) *Attorney, Agent, or Firm* — BakerHostetler

(57) ABSTRACT

An ophthalmic microscope including an observation optical system having a first focal point in front of an eye; an objective auxiliary lens positionable on the eye side of an objective lens in the observation optical system or releasable therefrom, a focal point when the objective auxiliary lens is positioned to a second focal point on an anterior ocular eye position; and a front lens positionable further toward the eye side than the first focal point or releasable from the position, a focal point through the eye's crystalline lens when the front lens is set to a third focal point and a posterior ocular segment position of the eye, the objective auxiliary lens set and the front lens released during anterior ocular segment observation, the front lens set and the objective auxiliary lens released during posterior ocular segment observation, without changing a positional relationship between the objective lens and eye.

7 Claims, 17 Drawing Sheets

(58) Field of Classification Search
USPC .......................................................... 351/205
See application file for complete search history.

(56) References Cited

OTHER PUBLICATIONS

International Preliminary Report on Patentability and Written Opinion issued in PCT/JP2018/031844, dated Mar. 12, 2020.

* cited by examiner

OPHTHALMIC MICROSCOPE

The present U.S. patent application is a U.S. National Phase Application under 35 U.S.C. 371 of International Application PCT/JP2018/031844 filed on Aug. 28, 2018, which claims priority to Japanese Patent Application Nos. JP 2017-165187 filed Aug. 30, 2017; JP 2017-167793 filed Aug. 31, 2017; and JP 2018-090269 filed May 8, 2018, the entire disclosures of which are incorporated herein by reference.

TECHNICAL FIELD

The present invention relates to an ophthalmic microscope with a function of switchably performing anterior ocular segment observation (e.g. observation of the cornea, anterior capsule, sclera or the like) and posterior ocular segment observation (e.g. observation of the retina) with respect to a subject eye, and relates, in particular, to an ophthalmic microscope which can perform anterior ocular segment observation and posterior ocular segment observation without changing a positional relationship between an objective lens and a subject eye.

In addition, the present invention relates to an OCT function expansion unit for adding an OCT measurement optical system (OCT: Optical Coherence Tomography) to an observation optical system of an ophthalmic microscope, and relates to an OCT function expansion unit capable of effecting switching between anterior ocular segment observation and posterior ocular segment observation without changing the positional relationship between the objective lens and the subject eye by the addition of the OCT function expansion unit.

BACKGROUND ART

The ophthalmic microscope is an apparatus for medical use or examination, which is capable of illuminating a patient's subject eye by an illumination optical system, and observing the subject eye by enlarging the subject eye by an observation optical system composed of a lens, etc.

There is known an ophthalmic microscope including a function of observing an anterior ocular segment (e.g. the cornea, anterior capsule, sclera or the like), and a function of observing a posterior ocular segment (e.g. the retina).

In this kind of ophthalmic microscope, when anterior ocular segment observation is performed, as illustrated in FIG. 16(A), an objective lens 71 and a subject eye 72 are relatively disposed such that an anterior ocular segment of the subject eye is positioned at a focal point 70 of an observation optical system.

On the other hand, when posterior ocular segment observation is performed, as illustrated in FIG. 16(B), the relative position between the objective lens 71 and subject eye 72 is changed such that the distance therebetween increases, and a front lens 74 is disposed between the subject eye 72 and the focal point 70. The characteristics and position of the front lens are selected such that a focal point is formed on the retina 722 via the crystalline lens 721 of the subject eye 72.

Note that in FIG. 16(A) and FIG. 16(B), the optical axis of a right-side observation optical system and the optical axis of a left-side observation optical system are denoted by O-R and O-L.

Besides, there are known various kinds of ophthalmic microscopes in which OCT functions are incorporated.

As illustrated in FIG. 17 (a drawing in which FIG. 1 of patent document 1 is cited), an ophthalmic microscope includes an observation optical system composed of lens groups 130, 140, 150, 170 and 180 including pairs of left and right lenses through which an optical axis of a left-eye observation optical system and an optical axis of a right-eye observation optical system are passed; one objective lens 110 through which the optical axis of the left-eye observation optical system and the optical axis of the right-eye observation optical system are commonly passed; an OCT measurement optical system 200, 250, 450, 460, 470; and an illumination optical system 310, 320, 330. In the OCT measurement optical system, output light from an OCT light source 200 travels through an optical fiber 250 and is emitted, and, after the direction of the output light is controlled by two scanning mirrors 450 and 460, the output light is made confluent with illumination light from an illumination optical system in a beam combiner 340, and the confluent light is reflected by a beam splitter 120 and made incident on a subject eye 1000.

In the ophthalmic microscope illustrated in FIG. 17, a tomographic image of the retina, cornea, anterior capsule, sclera or the like of the subject eye can be acquired, and not only a surface of a tissue but also a state of the inside of the tissue can be observed. Thereby, the precision of diagnosis of a disease of the eye can be enhanced, and the rate of success of ophthalmic surgery can be increased.

PRIOR ART REFERENCES

Patent Documents

Patent Document 1: JP H8-66421 A

DISCLOSURE OF THE INVENTION

Problems to be Solved by the Invention

In the conventional ophthalmic microscope as illustrated in FIG. 17, however, the distance between the ophthalmic microscope and the subject eye has to be changed between a time when the retina is observed or an OCT tomographic image of the retina is acquired, and a time when the cornea, anterior capsule, sclera or the like is observed or an OCT tomographic image of the cornea, anterior capsule, sclera or the like is acquired, and such a problem arises that the efficiency of an examination, treatment or the like deteriorates.

Thus, in consideration of the situation of the conventional art, an object of the present invention is to provide an ophthalmic microscope which is capable of observing, and acquiring a tomographic image of, an anterior ocular segment and a posterior ocular segment without changing a positional relationship between an objective lens and a subject eye.

Another object of the invention is to provide a function expansion unit which is capable of incorporating, into an ophthalmic microscope of existing specifications, a function capable of observing, and acquiring a tomographic image of, an anterior ocular segment and a posterior ocular segment without changing a positional relationship between an objective lens and a subject eye.

Means for Solving the Problems

In order to solve the problems, the inventors of the present application, as a result of tremendous research effort, have arrived at the present invention, based on the knowledge that, in an ophthalmic microscope, observation of an anterior ocular segment and observation of a posterior ocular segment can be performed without changing the positions of the ophthalmic microscope and a subject eye, by changing the position of a focal point of an observation optical system along the optical axis between a time when the anterior ocular segment (e.g. the cornea, anterior capsule, sclera or the like) is observed and a time when the posterior ocular segment (e.g. the retina) is detected.

In addition, the inventors have arrived at the invention of a function expansion unit, based on the knowledge that when an OCT measurement optical system is assembled as a detachable unit in an ophthalmic microscope of existing specifications, a function of changing the position of a focal point of an observation optical system along the optical axis is incorporated into the unit, and thereby there can be provided an ophthalmic microscope capable of OCT measurement, which can observe the anterior ocular segment and can acquire a tomographic image of the posterior ocular segment without changing the positions of the ophthalmic microscope and the subject eye.

Specifically, the outline of the ophthalmic microscope of the present invention is as follows.

(1) An ophthalmic microscope with a function of switchably performing anterior ocular segment observation (e.g. observation of the cornea, anterior capsule, sclera or the like) and posterior ocular segment observation (e.g. observation of the retina) with respect to a subject eye, including:

an observation optical system having a first focal point in front of the subject eye;

an objective auxiliary lens configured to be capable of being set in a position on the subject eye side of an objective lens (between an objective lens and the subject eye, and further toward the objective lens side than focal point) in the observation optical system or on a side opposite to the subject eye side, or capable of being released from the position, a focal point at a time when the objective auxiliary lens is set being set to a second focal point which is an anterior ocular segment position of the subject eye; and a front lens configured to be capable of being set in a position further toward the subject eye side than the first focal point (a position between the first focal point and the subject eye) or being released from the position, a focal point through the crystalline lens (including an artificial crystalline lens) of the subject eye at a time when the front lens is set being set to a third focal point which is a posterior ocular segment position of the subject eye, wherein the objective auxiliary lens is set and the front lens is released during the anterior ocular segment observation, without changing a positional relationship between the objective lens and the subject eye, and the front lens is set and the objective auxiliary lens is released during the posterior ocular segment observation, without changing the positional relationship between the objective lens and the subject eye.

(2) The ophthalmic microscope according to (1), further including an OCT measurement optical system, the OCT measurement optical system including an OCT measurement optical system objective lens.

(3) The ophthalmic microscope according to (2), wherein the OCT measurement optical system further includes:

a first optical member configured to guide light from an OCT light source in a first optical axis direction;

a first reflecting member configured to guide the light guided in the first optical axis direction in a second optical axis direction substantially orthogonal to the first optical axis direction;

a second optical member configured to relay the light guided in the second optical axis direction; and a second reflecting member configured to guide the light relayed by the second optical member in a third optical axis direction substantially orthogonal to the second optical axis direction, and the OCT measurement optical system objective lens is disposed on the third optical axis direction and radiates the light guided in the third optical axis direction onto a predetermined portion of the subject eye.

(4) The ophthalmic microscope according to (2) or (3), wherein the observation optical system includes the objective lens having such a shaped that a part of a circular lens is cut off (in such a manner to include a cut surface parallel to the optical axis), the OCT measurement optical system includes the OCT measurement optical system objective lens which is disposed in the cut-off part of the objective lens, has a first focal point in front of the subject eye, and is configured such that an optical path of OCT measurement light passes through the objective auxiliary lens, when the objective auxiliary lens is set and the front lens is released, a focal point is set to a second focal point which is an anterior ocular segment position of the subject eye, and OCT measurement of the anterior ocular segment is performed, and when the front lens is set and the objective auxiliary lens is released, a focal point is set to a third focal point which is a posterior ocular segment position of the subject eye, and OCT measurement of the posterior ocular segment is performed.

(5) The ophthalmic microscope according to any one of (1) to (4), further including a mechanism configured such that the front lens is released when the objective auxiliary lens is set, and the objective auxiliary lens is released when the front lens is set.

(6) The ophthalmic microscope according to any one of (1) to (5), wherein the objective auxiliary lens is a concave lens.

(7) The ophthalmic microscope according to any one of (1) to (6), wherein the ophthalmic microscope includes a plurality of kinds of the front lenses, and a plurality of kinds of the objective auxiliary lenses corresponding to the front lenses.

(8) An OCT function expansion unit configured to add an OCT measurement optical system to an ophthalmic microscope main body which includes a front lens capable of being set on or released from an optical path of an observation optical system, thereby being capable of effecting switching between anterior ocular segment observation and posterior ocular segment observation with respect to a subject eye, the OCT function expansion unit including:

a replacement objective lens for replacement of an objective lens of the observation optical system of the microscope main body, wherein the replacement objective lens has such a shape that a part of a circular lens is cut off, an OCT measurement optical system objective lens is provided in the cut-off part of the replacement objective lens, the observation optical system, in which the objective lens is replaced with the replacement objective lens, and the OCT measurement optical system have a first focal point in front of the subject eye, an objective auxiliary lens is provided which is configured to be capable of being set in a position located further toward the subject eye side than the replacement objective lens and the OCT measurement optical system objective lens or located on an opposite side to the subject eye, or capable of being released from the position, a focal point at a time when the objective auxiliary lens is set being set to a second focal point which is an anterior ocular segment position of the subject eye, when the front lens is set in a position further toward the subject eye side than the first focal point, a focal point through the crystalline lens of the subject eye is set to a third focal point which is a posterior ocular segment position of the subject eye, the objective auxiliary lens is set and the front lens is released during the anterior ocular segment observation, and the front lens is set and the objective auxiliary lens is released during the posterior ocular segment observation, whereby switching between the anterior ocular segment observation and the posterior ocular segment observation by the observation optical system and the OCT measurement optical system is enabled without changing a positional relationship between the objective lens and the subject eye.

(9) The OCT function expansion unit according to (8), wherein the OCT measurement optical system includes:

a first optical member configured to guide light from an OCT light source in a first optical axis direction;

a first reflecting member configured to guide the light guided in the first optical axis direction in a second optical axis direction substantially orthogonal to the first optical axis direction;

a second optical member configured to relay the light guided in the second optical axis direction; and a second reflecting member configured to guide the light relayed by the second optical member in a third optical axis direction substantially orthogonal to the second optical axis direction, and the OCT measurement optical system objective lens is disposed on the third optical axis direction and radiates the light guided in the third optical axis direction onto a predetermined portion of the subject eye.

Effect of the Invention

Observation of, and acquisition of a tomographic image of, an anterior ocular segment and a posterior ocular segment can be performed without changing the positional relationship between an objective lens and a subject eye.

By the OCT function expansion unit, a function capable of observing, and acquiring a tomographic image of, the anterior ocular segment and the posterior ocular segment, without changing the positional relationship between the objective lens and the subject eye, can be incorporated in an ophthalmic microscope of existing specifications.

DESCRIPTION OF EMBODIMENTS

Figure 1:
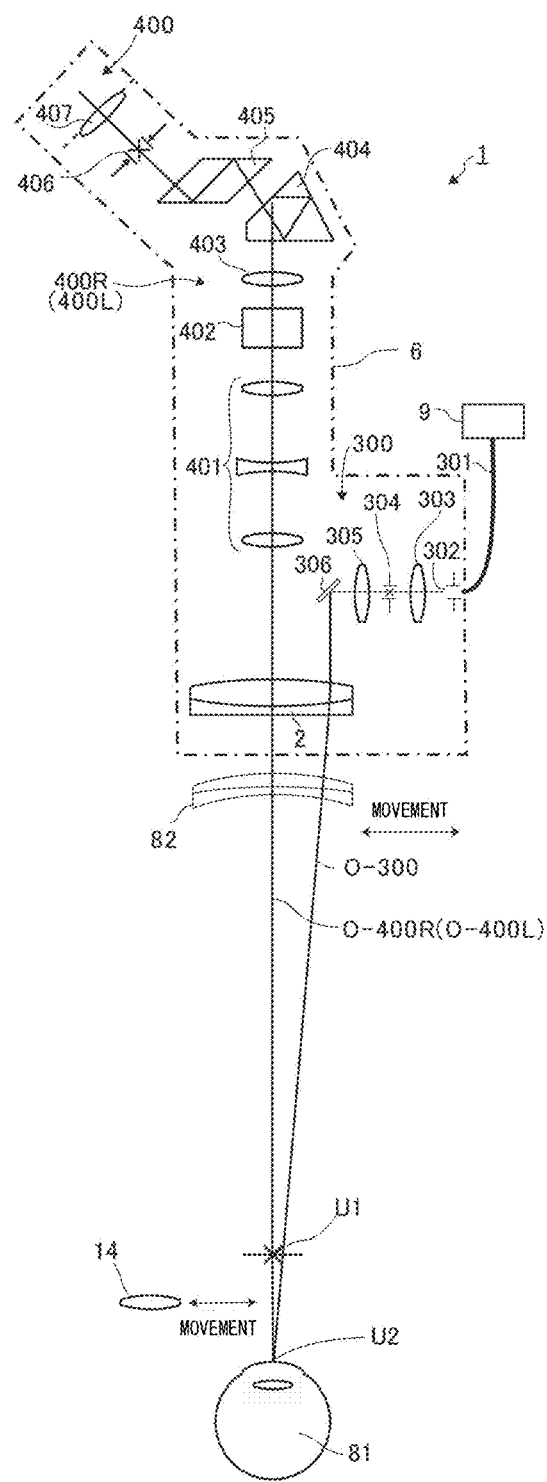
FIG. 1 is a schematic side view illustrating an ophthalmic microscope of a first embodiment of the present invention, which does not include an OCT measurement optical system, at a time of observing an anterior ocular segment.

1. Ophthalmic Microscope of the Present Invention

In an ophthalmic microscope of the present invention, an observation optical system is configured to include optical elements such as a lens, a prism, etc., which enable observation of a subject eye by return light which is reflected/scattered from the subject eye that is illuminated by an illumination optical system. In the present invention, the observation optical system can include a left-eye observation optical system and a right-eye observation optical system, and, when parallax is caused in images acquired by the left and right observation optical systems, stereoscopic observation can be performed by binocular vision.

In addition, the observation optical system of the present invention may be an observation optical system which can directly observe a subject eye by an observer's naked eyes through eyepieces, ocular lenses or the like, or may be an observation optical system which receives reflective light or the like from the subject eye by an imaging device (CCD) or the like and can cause a display to display the received reflective light or the like, or may be an observation optical system which enables direct observation by the naked eyes and enables display on the display.

The observation optical system composed of the left-eye observation optical system and right-eye observation optical system includes an objective lens through which the optical axis of the left-eye observation optical system and the optical axis of the right-eye observation optical system pass commonly.

In the present invention, the objective lens is, for example, a lens assembled on the subject eye side in an ophthalmic microscope main body.

The front lens (loupe), when used, is detachably inserted between the objective lens and the subject eye (near the subject eye), and is not referred to as "objective lens" in the present invention.

Note that the illumination optical system is configured to include an optical element which illuminates the subject eye. The illumination optical system may be configured to guide natural light to the subject eye, but, in usual cases, is configured to include an illumination light source and to guide light from the illumination light source to the subject eye. The illumination optical system can be configured to include the objective lens included in the above-described observation optical system.

The microscope optical system of the present invention can include a collimator (an optical member for OCT interface) which takes in light from an OCT light source provided in an OCT apparatus and sends back return light from the subject eye, on which the light from the OCT light source is radiated, to the OCT apparatus. In this case, the microscope optical system can include an OCT measurement optical system, and can also include an OCT reference light optical system, and furthermore the OCT light source can be assembled in the microscope optical system.

In the microscope optical system of the present invention, a part of the objective lens of the observation optical system can be removed, and an objective lens of the OCT measurement optical system is provided in the removed part.

By this configuration, in the microscope optical system of the present invention, the OCT measurement optical system is independent from the observation optical system. Accordingly, when making optical design of the microscope optical system of the present invention, there is no need to consider mutual influence between the observation optical system and the OCT measurement optical system.

Thereby, the microscope optical system of the present invention can bring about such an advantageous effect that the degree of freedom of optical design is enhanced.

For example, by separately executing position control of the objective lens of the observation optical system and the OCT measurement optical system objective lens, such optical design can be implemented that the focal point of the observation optical system and the focal point of the OCT measurement optical system can independently be adjusted.

Note that an XY scanning mechanism and a Z scanning mechanism can be mounted on a measurement light optical path of the OCT measurement optical system. These mechanisms can be fabricated by, for example, MEMS.

In addition, the OCT measurement optical system can be detachably assembled as one unit in the observation optical system. Note that, by assembling a plurality of OCT measurement optical systems in the microscope optical system, such optical design is possible that a more detailed three-dimensional tomographic image of an observation target can be acquired.

In the present invention, as optical elements used in the observation optical system, illumination optical system and OCT measurement optical system, use can be made of, for example, a lens, a prism, a mirror, an optical filter, a diaphragm, a diffraction grating, a polarizer element, and the like.

In the present invention, the ophthalmic microscope is an apparatus for medical use or examination, which enables visual observation of the subject eye by enlarging the subject eye, and includes not only an ophthalmic microscope for humans, but also an ophthalmic microscope for animals.

The "ophthalmic microscope" is not limited to these, and includes, for example, a fundus camera, a slit lamp, an ophthalmic surgery microscope, and the like.

2. First Embodiment

Hereinafter, an example of an ophthalmic microscope (hereinafter, simply referred to as "microscope") according to an embodiment of the present invention will be described with reference to the accompanying drawings.

Figure 2:
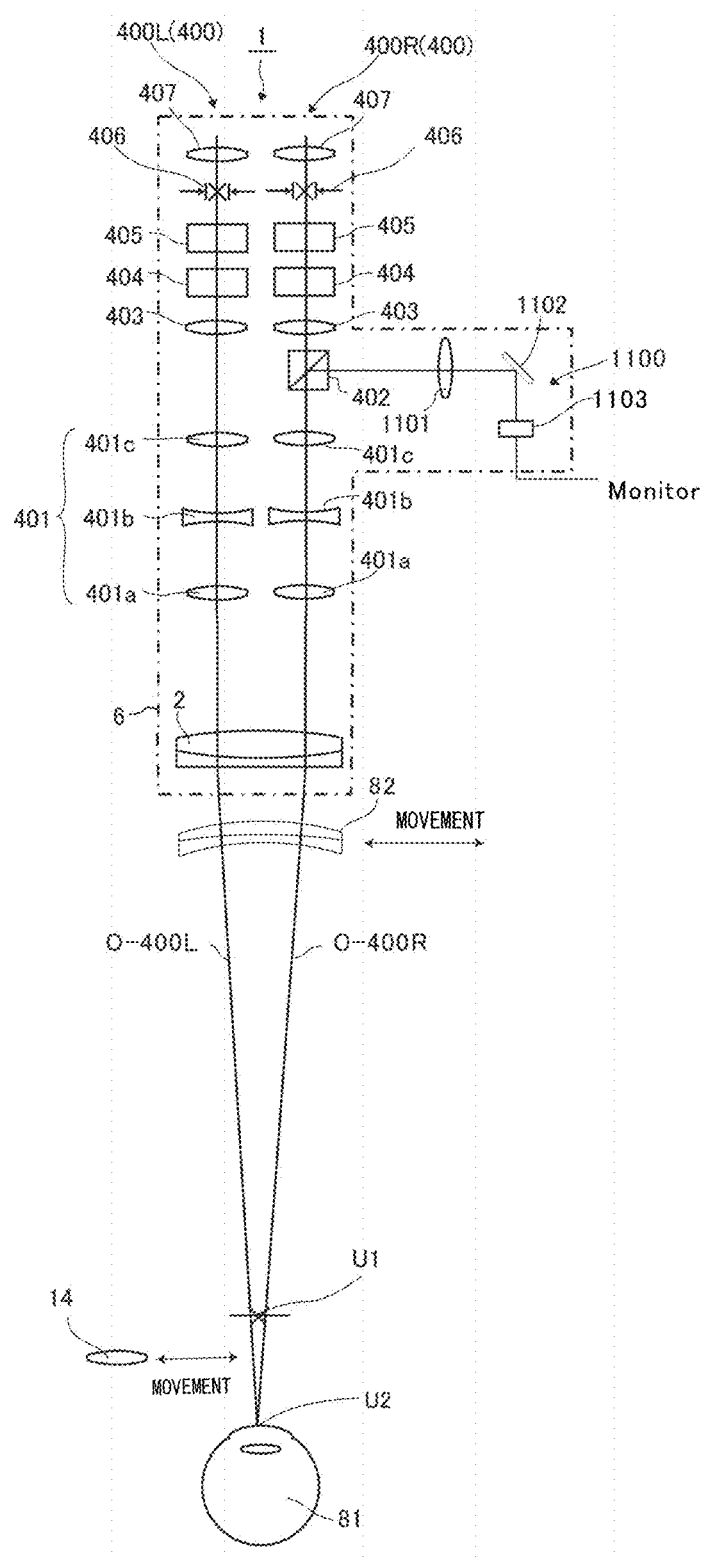
FIG. 2 is a schematic front view illustrating the ophthalmic microscope of the first embodiment of the present invention, which does not include an OCT measurement optical system, at a time of observing the anterior ocular segment.
Figure 3:
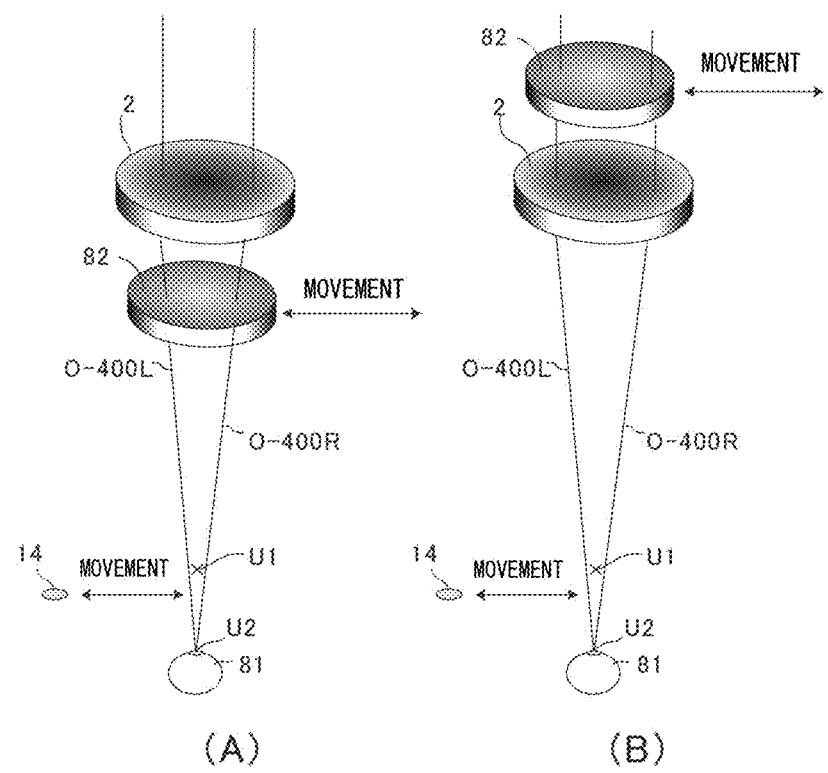
FIG. 3(A) is a schematic view illustrating an observation optical system (an observation optical system in which an objective auxiliary lens is provided on a subject eye side of an objective lens for observation) of the ophthalmic microscope illustrated in FIG. 1 and FIG. 2 at a time of observing the anterior ocular segment.
FIG. 3(B) is a schematic view illustrating an observation optical system in which the objective auxiliary lens is provided on a side opposite to the subject eye side of the objective lens for observation.

FIG. 1 is a schematic side view of a microscope 1 which includes an observation function but does not include an OCT function (tomographic photography function), and FIG. 2 is a schematic front view of the microscope 1, FIG. 1 and FIG. 2 illustrating a state in which an anterior ocular segment (e.g. the cornea, anterior capsule, sclera or the like) of a subject eye 81 is observed. In addition, FIG. 3(A) is a schematic view illustrating an observation optical system 400 (an observation optical system in which an objective auxiliary lens is provided on a subject eye side of an objective lens for observation) of the microscope of in FIG. 1 and FIG. 2.

As illustrated in FIG. 1, the microscope 1 includes an illumination optical system 300 (not illustrated in FIG. 2) in addition to the observation optical system 400.

The observation optical system 400 can observe the retina of an observation target (the subject eye 81 in FIG. 1 and FIG. 2). As referred to in FIG. 1, the illumination optical system 300 can illuminate that part of the subject eye 81, which is to be observed.

In FIG. 1 and FIG. 2, the observation optical system has a first focal point U1 in front of the subject eye 81.

As explicitly illustrated in FIG. 2, the observation optical system 400 includes a right-eye observation optical system 400R and a left-eye observation optical system 400L. Note that FIG. 1 illustrates an entire configuration with respect to the right-eye observation optical system 400R, and illustrates only an objective lens 2 that is shared with the right-eye observation optical system 400R with respect to the left-eye observation optical system 400L.

In addition, as explicitly illustrated in FIG. 2, an optical axis O-400R of the right-eye observation optical system 400R and an optical axis O-400L of the left-eye observation optical system 400L pass through the objective lens 2.

In the present embodiment, the illumination optical system 300 and the observation optical system 400 are accommodated in a microscope main body 6. In FIG. 1 and FIG. 2, the microscope main body 6 is indicated by a dot-and-dash line.

The illumination optical system 300 illustrated in FIG. 1 is configured to include an illumination light source 9, an optical fiber 301, an emission light diaphragm 302, a condenser lens 303, an illumination field diaphragm 304, a collimate lens 305 and a reflection mirror 306. An optical axis of the illumination optical system 300 is indicated by O-300.

As illustrated in FIG. 1, the illumination light source 9 is provided outside the microscope main body 6 in the present embodiment. One end of the optical fiber 301 is connected to the illumination light source 9. The other end of the optical fiber 301 is disposed in such a position of the microscope main body 6 as to face the emission light diaphragm 302. Illumination light emitted from the illumination light source 9 is guided by the optical fiber 301, and is made incident on the condenser lens 303 via the emission light diaphragm 302.

The emission light diaphragm 302 functions to shut off a partial area of an emission aperture of the optical fiber 301. When the shut-off area by the emission light diaphragm 302 is varied, the emission area of illumination light is varied. Thereby, a radiation angle by illumination light, i.e. an angle between an incidence direction of illumination light to the subject eye 81 and the optical axis of the objective lens 2, can be changed.

The illumination field diaphragm 304 is provided at an optically conjugate position (a position of x) with the first focal point U1 of the objective lens 2. The collimate lens 305 converts the illumination light, which has passed through the illumination field diaphragm 304, to a parallel beam. The reflection mirror 306 reflects the illumination light, which is converted to the parallel beam by the collimate lens 305, toward the objective lens 2 for observation. The light reflected by the reflection mirror 306 passes through the objective lens 2 and is radiated on the subject eye 81.

The illumination light radiated on the subject eye 81 is reflected/scattered by a tissue of the anterior ocular segment. The reflected/scattered return light (also called "observation light") passes through the objective lens 2 and is incident on the observation optical system 400.

The observation optical system 400 is used in order to observe via the objective lens 2 the subject eye 81 which is illuminated by the illumination optical system 300.

As illustrated in FIG. 1 and FIG. 2, the observation optical system 400 is configured to include a variable power lens system 401 (lenses 401a, 401b and 401c), a beam splitter 402 (a beam splitter for acquiring image information for TV camera display), an imaging lens 403, an image erecting prism 404, an interpupillary distance adjusting prism 405, a view field diaphragm 406, and an ocular lens 407. An optical axis of the observation optical system 400 is indicated by O-400.

As illustrated in FIG. 2, the beam splitter 402 of the right-eye observation optical system 400R separates part of the observation light, which is guided from the subject eye 81 along the right-eye observation optical system, and guides the separated part to a photographing optical system 1100. The photographing optical system 1100 is configured to include an imaging lens 1101, a reflection mirror 1102, and a TV camera 1103. Image information which the TV camera 1103 acquires is sent to a monitor that is not illustrated, and is displayed on the monitor.

As illustrated in FIG. 1 and FIG. 2, the image erecting prism 404 converts an inverted image to an erected image. The interpupillary distance adjusting prism 405 is an optical element for adjusting a distance between left and right observation optical paths in accordance with an observer's interpupillary distance (a distance between the left eye and the right eye). The view field diaphragm 406 restricts the observer's view field by shutting off a peripheral area in a cross section of observation light. The view field diaphragm 406 is provided at a conjugate position (a position of x) with the first focal point U1 of the objective lens 2.

The right-eye observation optical system 400R and left-eye observation optical system 400L may be configured to include a stereovariator which is configured to be insertable/detachable in/from the optical path. The stereovariator is an optical axis position changing element for changing a relative position between the optical axes O-400L and O-400R of the left and right observation optical systems, which are guided by the left and right variable power lens systems 401. The stereovariator is evacuated, for example, to an evacuation position provided on the observer side with respect to the observation optical path.

In the microscope 1 of FIG. 1 and FIG. 2, the observation optical system has the first focal point (indicated by U1) in front of the subject eye 81, when no lens exists between the objective lens 2 and subject eye 81.

In the microscope 1, an objective auxiliary lens 82 is provided on the subject eye 81 side of the objective lens 2.

The objective auxiliary lens 82 can be set in a position close to the objective lens 2 between the first focal point U1 and the objective lens 2, or can be released from this position. The objective auxiliary lens 82 is selected such that the focal point at a time when the objective auxiliary lens 82 is set is a second focal point (U2) which is an anterior ocular segment position of the subject eye.

Note that FIG. 3(A) illustrates a case where the objective auxiliary lens 82 is provided on the subject eye 81 side of the objective lens 2 in the observation optical system at a time of observing the anterior ocular segment of the subject eye 81. In the present invention, as illustrated in FIG. 3(B), the objective auxiliary lens 82 may be provided on a side opposite to the subject eye 81 side of the objective lens 2, and the anterior ocular segment of the subject eye 81 can be observed.

Figure 4:
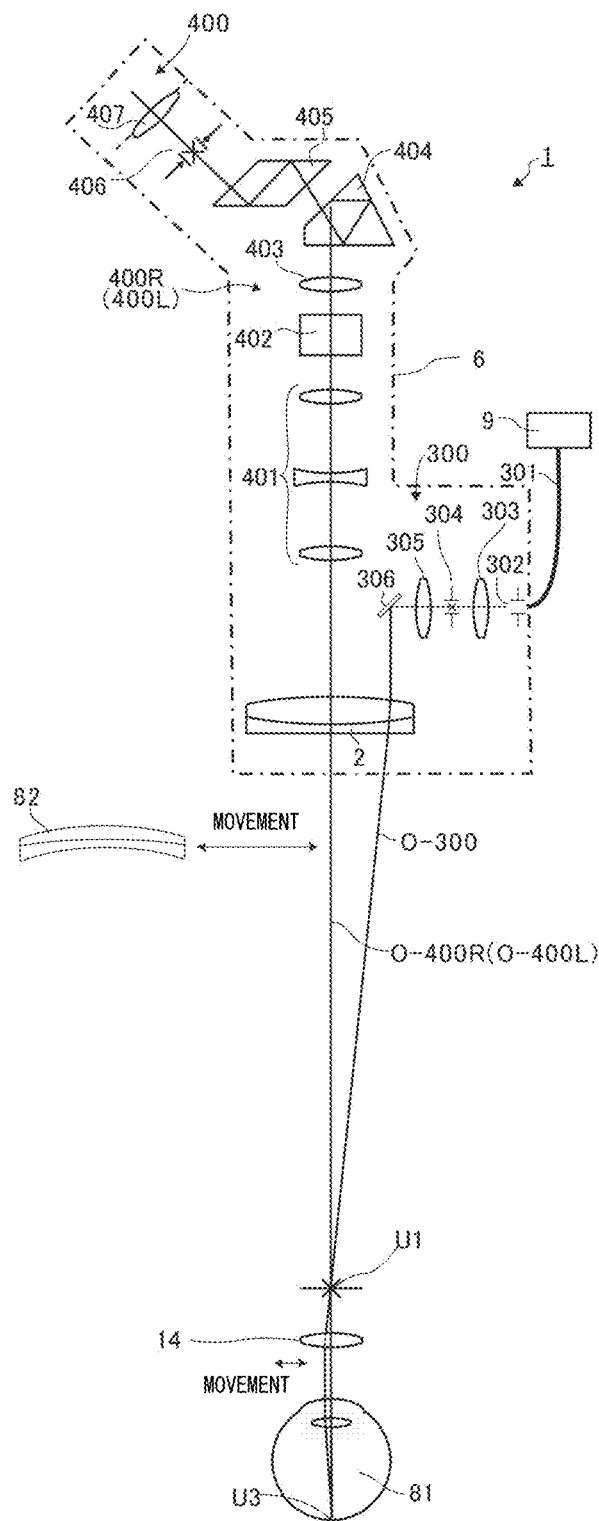
FIG. 4 is a schematic side view illustrating the ophthalmic microscope of the first embodiment of the present invention, which does not include an OCT measurement optical system, at a time of observing a posterior ocular segment.

FIG. 4 is a side view corresponding to FIG. 1 and illustrating a state in which a posterior ocular segment (e.g. the retina) of the subject eye 81 is observed in the apparatus described with reference to FIG. 1 and FIG. 2. Similarly, FIG. 5 is a front view corresponding to FIG. 2, and FIG. 6(A) is a schematic view corresponding to FIG. 3(A).

Figure 5:
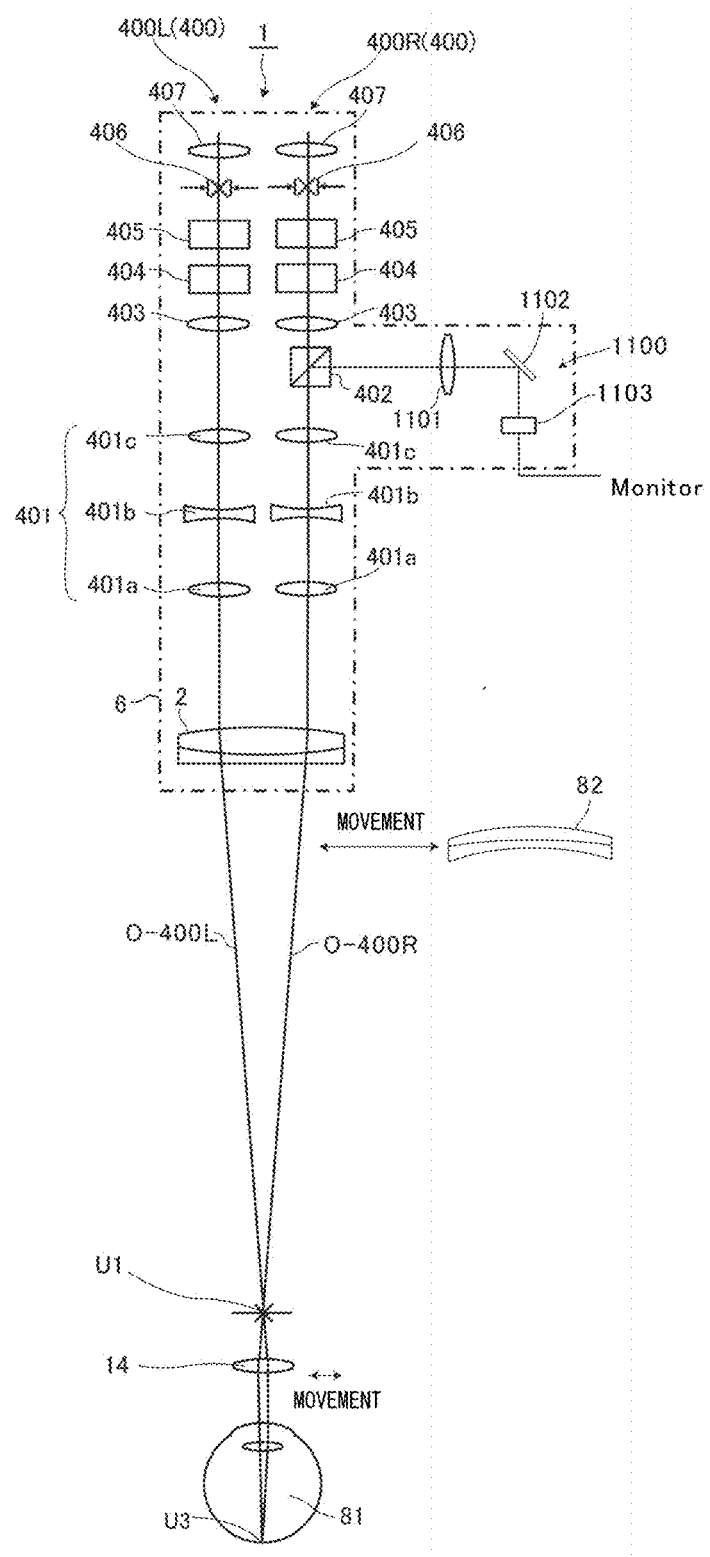
FIG. 5 is a schematic front view illustrating the ophthalmic microscope of the first embodiment of the present invention, which does not include an OCT measurement optical system, at a time of observing a posterior ocular segment.
Figure 6:
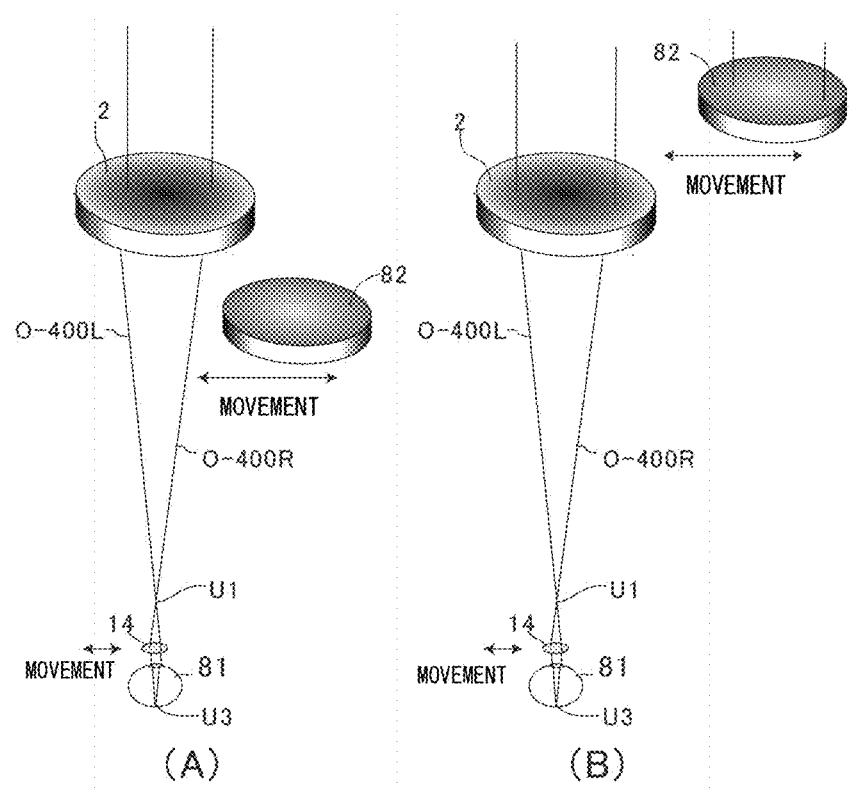
FIG. 6(A) is a schematic view illustrating an observation optical system (an observation optical system in which the objective auxiliary lens is provided on the subject eye side of the objective lens for observation) of the ophthalmic microscope illustrated in FIG. 4 and FIG. 5 at a time of observing the posterior ocular segment.
FIG. 6(B) is a schematic view illustrating an observation optical system in which the objective auxiliary lens is provided on the side opposite to the subject eye side of the objective lens for observation.

In FIG. 4 and FIG. 5, the front lens 14 is set in a position further toward the subject eye 81 side than the first focal point U1, and a focal point (third focal point U3) via the crystalline lens of the subject eye 81 at a time when the front lens 14 is set is located at a position (a posterior ocular segment position) of the retina of the subject eye 81.

Note that in the case where the objective auxiliary lens 82 is provided on a side opposite to the subject eye 81 side of the objective lens 2 (see FIG. 3(B)), when the posterior ocular segment of the subject eye 81 is observed, the objective auxiliary lens 82 needs to be released as illustrated in FIG. 6(B).

3. Second Embodiment

Hereinafter, an embodiment of the ophthalmic microscope 1 including an OCT function (tomographic photography function) will be described.

It is preferable that an OCT measurement optical system can be additionally assembled as an expansion function in an ophthalmic microscope including an observation optical system and an illumination optical system. In order to additionally assemble the OCT measurement optical system in this manner, the inventors have found that, by bending twice the optical path of the OCT measurement optical system, the OCT measurement optical system can be assembled compactly such that the OCT measurement optical system is adapted to the primary function of the microscope.

Specifically, the ophthalmic microscope of the present invention further includes an OCT measurement optical system, the OCT measurement optical system including:
- a first optical member configured to guide light from an OCT light source in a first optical axis direction;
- a first reflecting member configured to guide the light, which is guided in the first optical axis direction, in a second optical axis direction substantially orthogonal to the first optical axis direction;
- a second optical member configured to relay the light guided in the second optical axis direction; and
- a second reflecting member configured to guide the light, which is relayed by the second optical member, in a third optical axis direction substantially orthogonal to the second optical axis direction,
- wherein an OCT measurement optical system objective lens is preferably disposed on the third optical axis such that the light guided in the third optical axis direction is radiated on a predetermined portion of a subject eye.

By adopting this optical configuration, the OCT measurement optical system can be assembled compactly such that the OCT measurement optical system is adapted to the primary function of the microscope.

Hereinafter, referring to the drawings, a detailed description will be given of an example of the embodiment of the ophthalmic microscope of the present invention, which includes the OCT measurement optical system in which an optical path is bent twice.

FIG. 7 to FIG. 14 are drawings which schematically illustrate a second embodiment that is another example of the ophthalmic microscope of the present invention.

Figure 7:
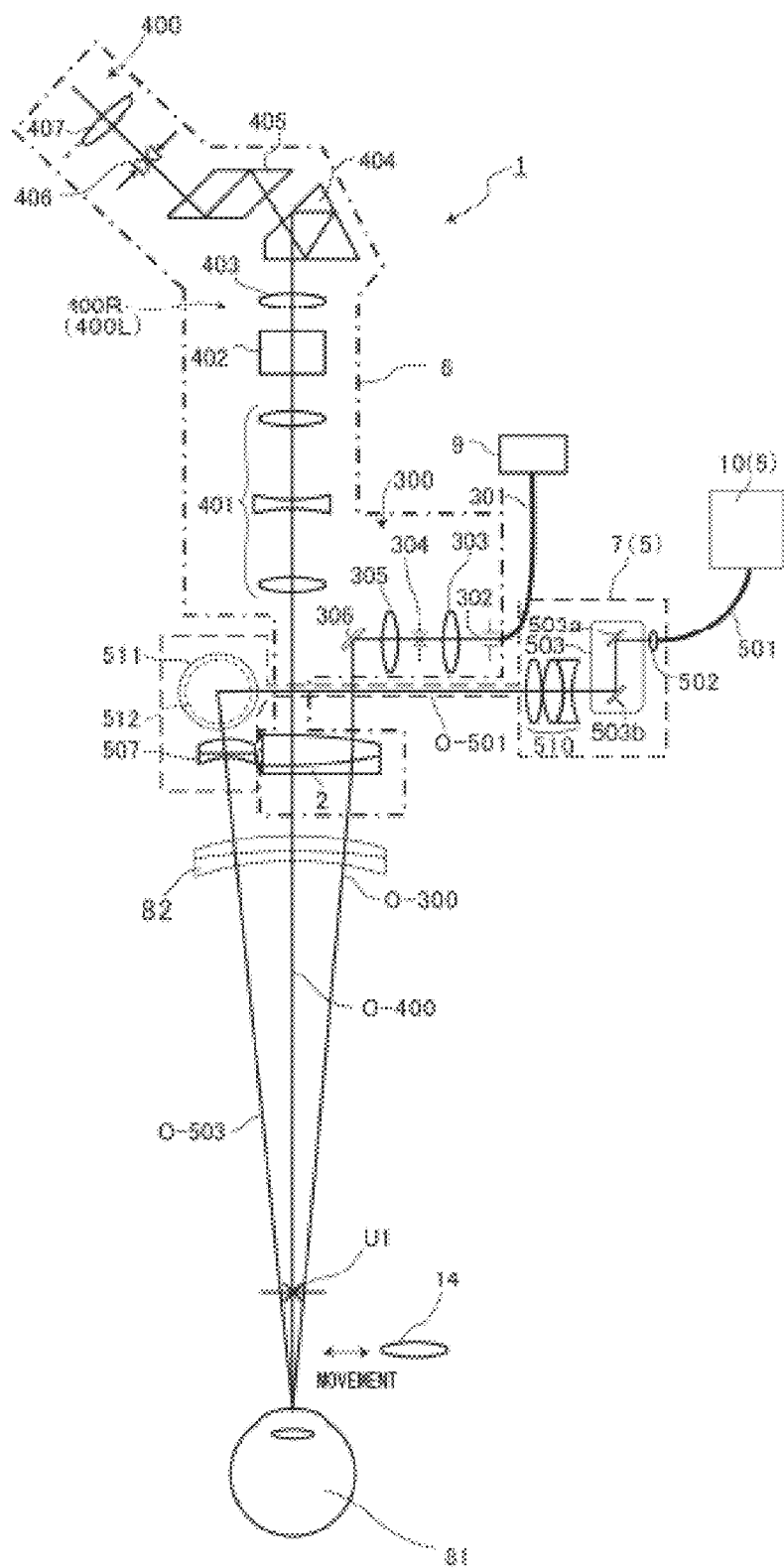
FIG. 7 is a schematic side view illustrating an ophthalmic microscope of a second embodiment of the present invention, which includes an OCT measurement optical system, at a time of observing an anterior ocular segment.
Figure 8:
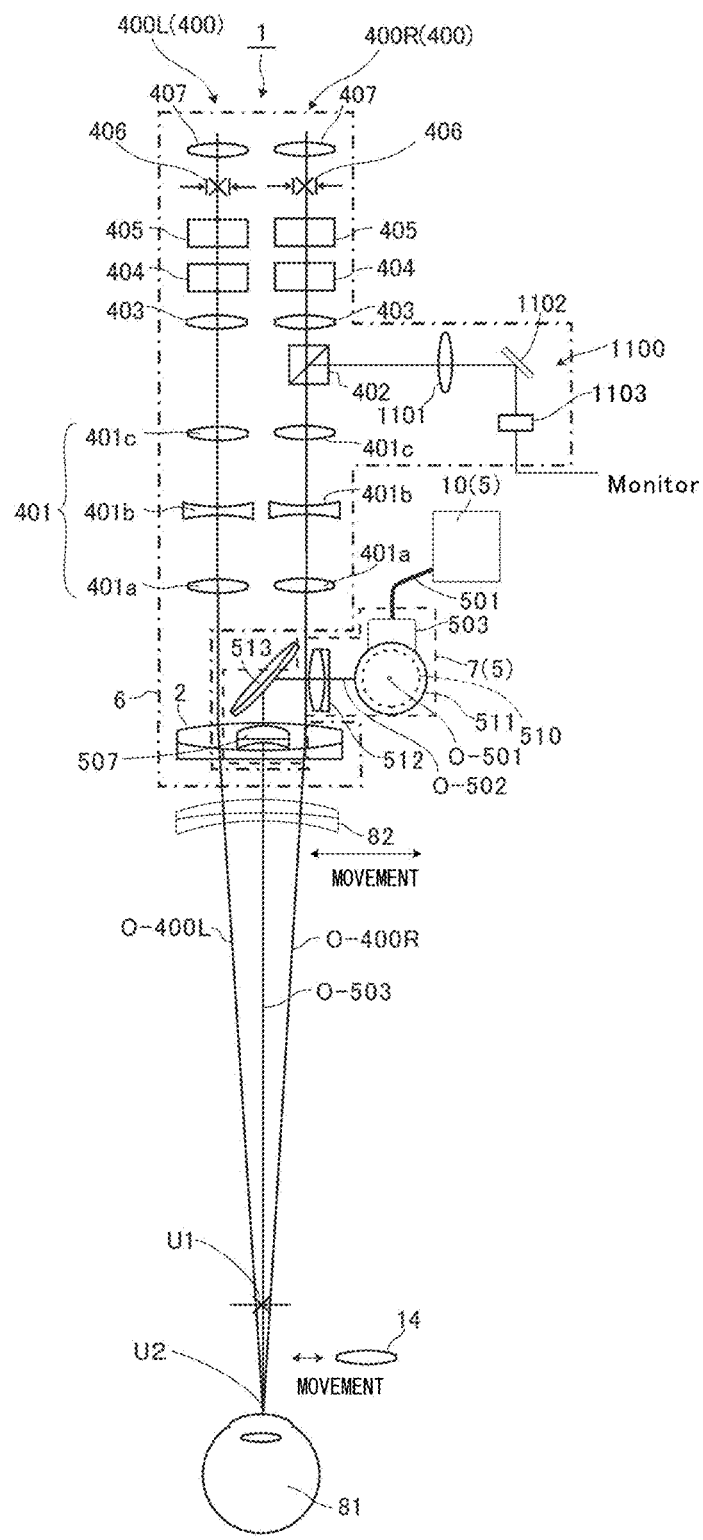
FIG. 8 is a schematic front view illustrating the ophthalmic microscope of the second embodiment of the present invention, which includes the OCT measurement optical system, at a time of observing the anterior ocular segment.
Figure 9:
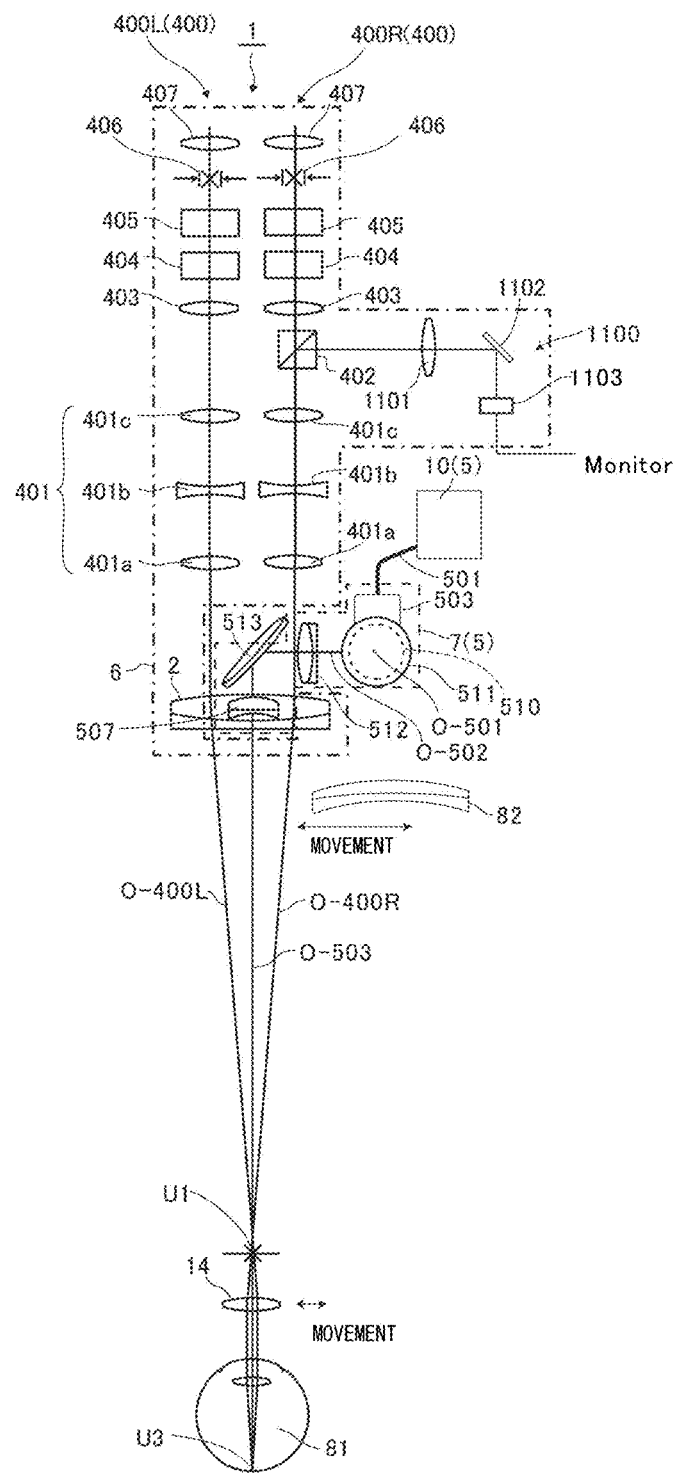
FIG. 9 is a schematic front view illustrating the ophthalmic microscope of the second embodiment of the present invention, which includes the OCT measurement optical system, at a time of observing a posterior ocular segment.

FIG. 7 is a schematic side view illustrating the ophthalmic microscope 1, and FIG. 8 is a schematic front view illustrating a case of observing an anterior ocular segment (e.g. the cornea, anterior capsule, sclera or the like). FIG. 9 is a schematic front view illustrating the ophthalmic microscope in a case of observing a posterior ocular segment (e.g. the retina).

As illustrated in FIG. 7, FIG. 8 and FIG. 9, the ophthalmic microscope 1 is equipped with an OCT apparatus 5.

The ophthalmic microscope 1 includes an illumination optical system 300 (not illustrated in FIG. 8 and FIG. 9), an observation optical system 400 and an OCT measurement optical system 500.

The observation optical system 400 can observe a predetermined portion of an observation target (the subject eye 81 in FIG. 7, FIG. 8 and FIG. 9). As referred to in FIG. 7, the illumination optical system 300 can illuminate that part of the subject eye 81, which is to be observed.

The OCT apparatus 5, with which the ophthalmic microscope 1 is equipped, can acquire a tomographic image of the subject eye 81. The OCT measurement optical system 500 is assembled in the ophthalmic microscope 1 as a part of the OCT apparatus 5. A reciprocal light guide path of measurement light is composed of the OCT measurement optical system 500, the front lens 14 and a reflection surface (the cornea, retina, or the like) of the subject eye 81.

As explicitly illustrated in FIG. 8 and FIG. 9, the observation optical system 400 includes a right-eye observation optical system 400R and a left-eye observation optical system 400L. Note that FIG. 7 illustrates an entire configuration with respect to the right-eye observation optical system 400R, and illustrates only an objective lens 2 that is shared with the right-eye observation optical system 400R with respect to the left-eye observation optical system 400L.

In addition, as explicitly illustrated in FIG. 8 and FIG. 9, an optical axis O-400R of the right-eye observation optical system 400R and an optical axis O-400L of the left-eye observation optical system 400L pass through the objective lens 2.

In the present embodiment, the illumination optical system 300 and the observation optical system 400 are accommodated in an ophthalmic microscope main body 6. Besides, the OCT measurement optical system 500 is accommodated in an OCT function expansion unit 7. In FIG. 7, FIG. 8 and FIG. 9, the ophthalmic microscope main body 6 is indicated by a dot-and-dash line, and the OCT function expansion unit 7 is indicated by a broken line.

The OCT function expansion unit 7 is detachably coupled to the ophthalmic microscope main body 6 by a joint unit that is not shown.

As illustrated in FIG. 7, FIG. 8 and FIG. 9, the OCT apparatus 5 is composed of an OCT unit 10 and the OCT function expansion unit 7.

The OCT measurement optical system 500 is accommodated in the OCT function expansion unit 7.

Figure 11:
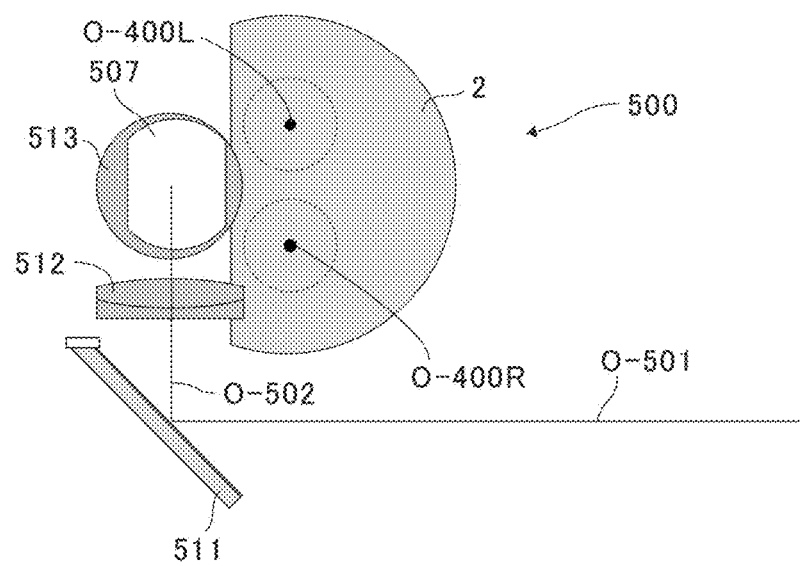
FIG. 11 is a plan view of the OCT measurement optical system illustrated in FIG. 10.
Figure 12:
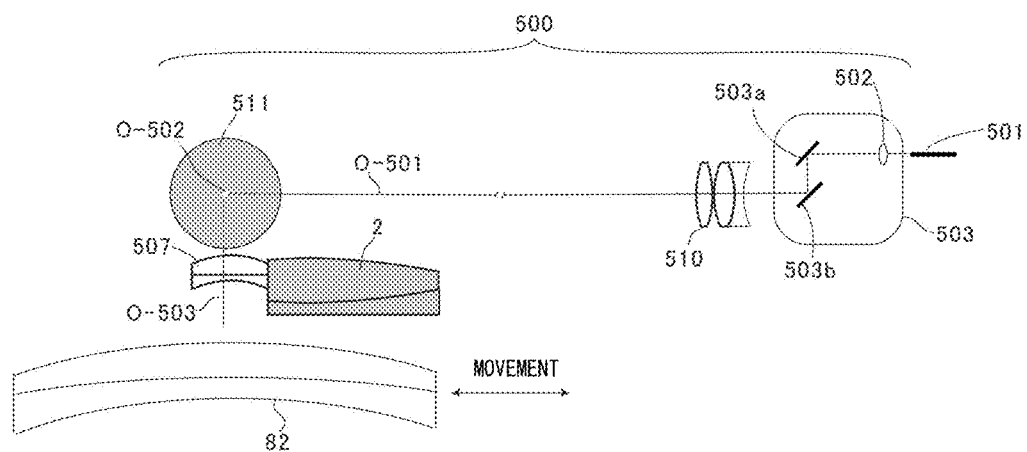
FIG. 12 is a side view of the OCT measurement optical system illustrated in FIG. 10.
Figure 13:
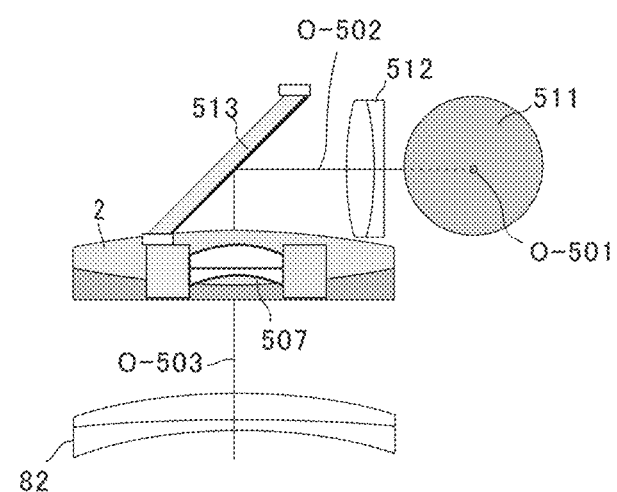
FIG. 13 is a front view of the OCT measurement optical system illustrated in FIG. 10.

FIG. 10(A) is a perspective view of the OCT measurement optical system 500 at a time of the configuration of FIG. 8, and FIG. 10(B) is a perspective view at a time of the configuration of FIG. 9. FIG. 11 is a plan view of the OCT measurement optical system 500, FIG. 12 is a side view of the same, and FIG. 13 is a front view of the same. Note that in FIG. 11 and FIG. 13, a collimate lens 502, a scanning function unit 503 and a first optical member 510 (to be described later) are not illustrated.

Figure 10:
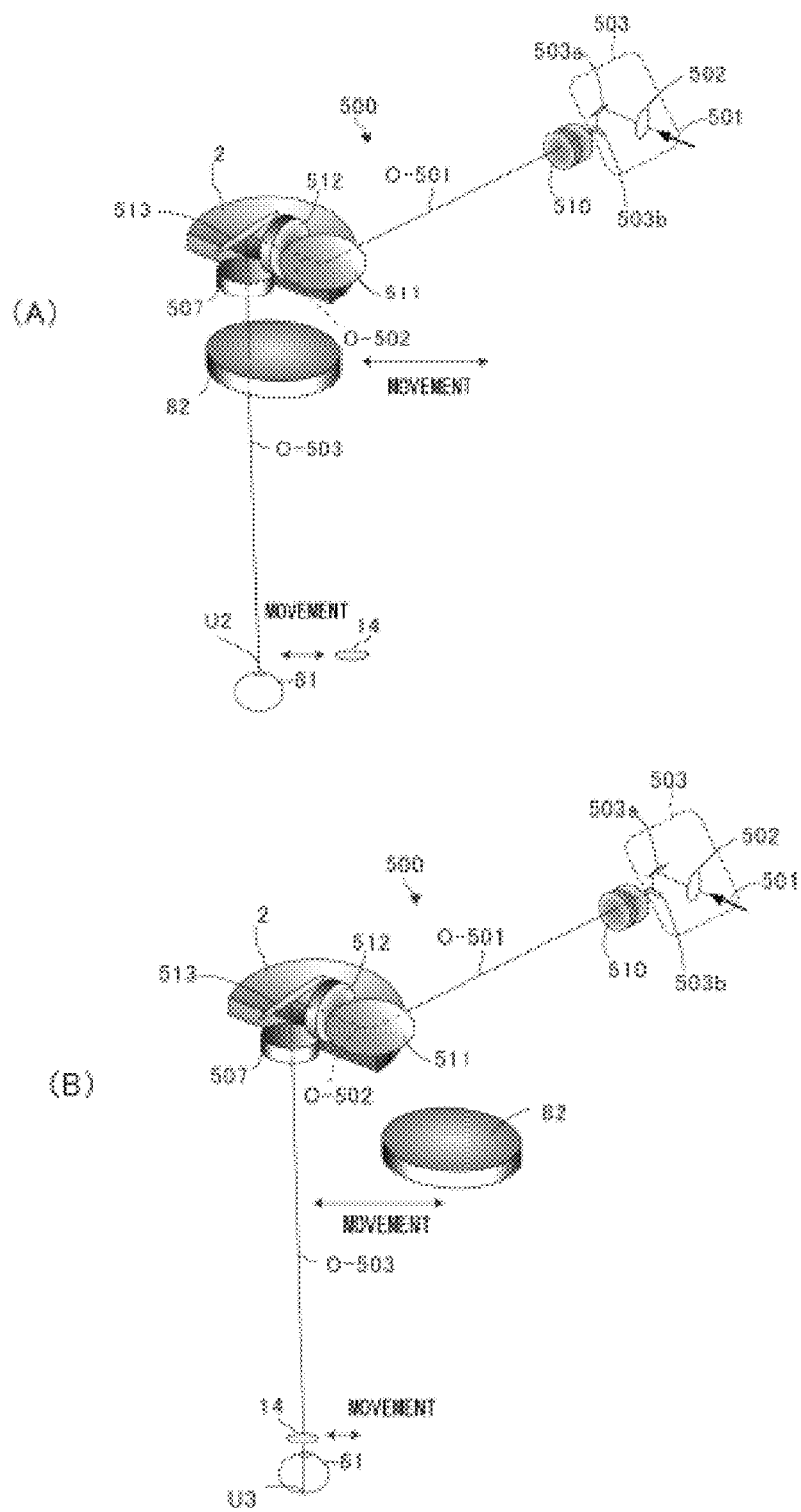
FIG. 10 is schematic views illustrating the OCT measurement optical system of the ophthalmic microscope of the second embodiment of the present invention, FIG. 10(A) being a schematic view illustrating the OCT measurement optical system at a time of observing an anterior ocular segment, and FIG. 10(B) being a schematic view illustrating the OCT measurement optical system at a time of observing a posterior ocular segment.

In FIG. 10 and FIG. 12, the OCT measurement optical system 500 is configured to include a collimate lens 502, a scanning function unit 503, a first optical member 510, a first reflecting member 511, a second optical member 512, a second reflecting member 513, and an OCT measurement optical system objective lens 507.

The scanning function unit 503 is a two-dimensional scanning mechanism including galvano mirrors 503a and 503b. The scanning function unit 503 is provided on a rear side (a side farther from the observer) of the ophthalmic microscope main body 6.

The first optical member 510 is an OCT imaging lens, and guides light, which is scanned by the scanning function unit 503, in a direction of a first optical axis O-501. When the ophthalmic microscope main body 6 is viewed from the front side, the first optical axis O-501 is formed from the depth side to the front side at a slightly outward position on the right side of the ophthalmic microscope main body 6, and the light scanned by the scanning function unit 503 is guided from the depth side toward the front side along the first optical axis O-501.

As illustrated in FIG. 10, FIG. 11, FIG. 12 and FIG. 13, the light guided along the first optical axis O-501 is guided by the first reflecting member 511 in a direction of a second optical axis O-502 which is orthogonal to the direction of the first optical axis O-501.

In the present embodiment, as referred to in FIG. 8 and FIG. 9, the second optical axis O-502 is formed from the rightward outside of the ophthalmic microscope main body 6 toward the inside.

The second optical member 512 is disposed on the second optical axis O-502, and light, which has passed through the second optical member 512, is reflected downward (in a direction substantially orthogonal to the second optical axis O-502) by the second reflecting member 513. This reflection optical path is indicated by a third optical axis direction O-503.

In the present embodiment, as illustrated in FIG. 7, the objective lens 2 is notched in a manner to have a cut surface which is substantially parallel to the optical axis O-400.

In the present embodiment, in this notched portion, the OCT measurement optical system objective lens 507 is accommodated.

The light guided by the third optical axis direction O-503 is focused at a predetermined position on the subject eye 81 side by the OCT measurement optical system objective lens 507.

In the present embodiment, as illustrated in FIG. 7, FIG. 8 and FIG. 9, a front-side focal point position (first focal point U1) of the objective lens 2 exists in front of the subject eye 81. When the objective auxiliary lens 82 is set on the first focal point U1 side of the objective lens 2, the front lens 14 is released (see FIG. 7, FIG. 8 and FIG. 10(A)). Conversely, when the objective auxiliary lens 82 is released on the first focal point U1 side of the objective lens 2, the front lens 14 is set (see FIG. 9 and FIG. 10(B)).

As described above, the optical axis O-503 of the OCT measurement optical system 500 extends through the OCT measurement optical system objective lens 507, and the optical axis O-503 of the OCT measurement optical system 500 is separated from the optical axis O-400 of the observation optical system 400.

Accordingly, the OCT measurement optical system 500 and the observation optical system 400 are independent from each other.

Figure 14:
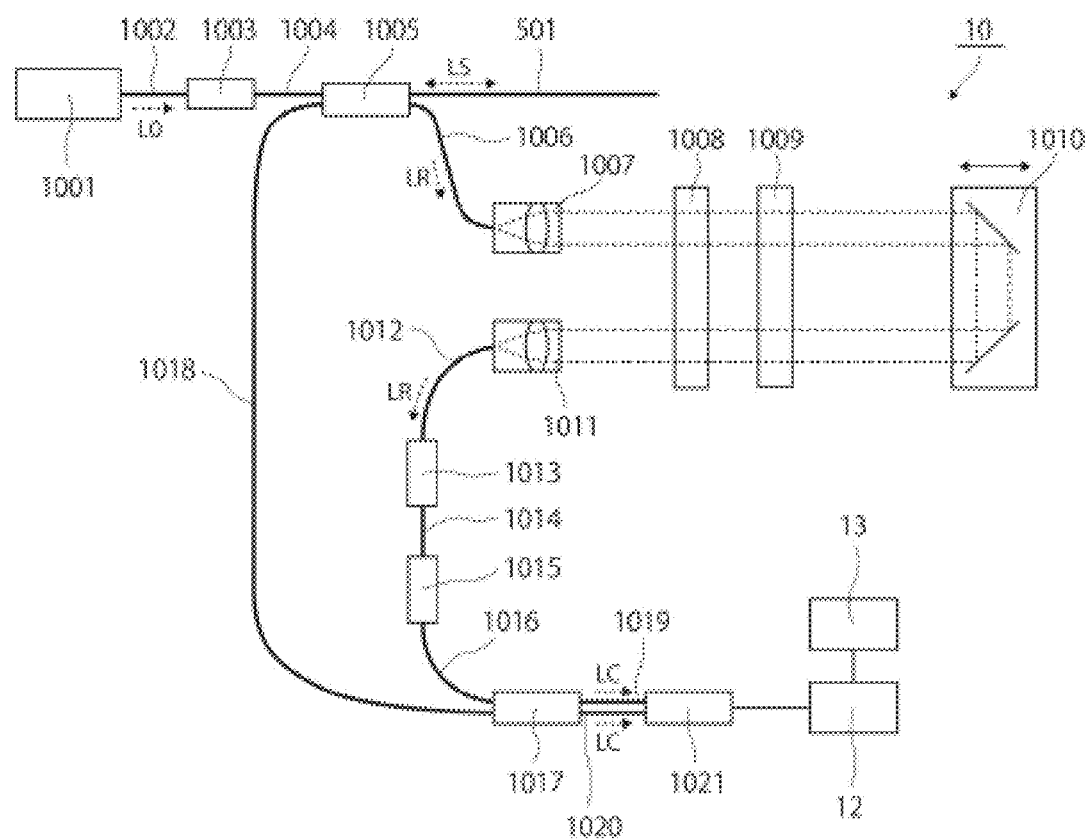
FIG. 14 is an explanatory view of an OCT apparatus for use in the ophthalmic microscope of the second embodiment of the present invention.

FIG. 14 is a drawing schematically illustrating an optical configuration of an OCT main body unit 10 for use in the microscope 1 of the present embodiment.

As illustrated in FIG. 14, the OCT main body unit 10 constitutes an interferometer which divides light L0 that is emitted from an OCT light source unit 1001 into measurement light LS and reference light LR, and which detects interference between the measurement light LS and reference light LR traveling through different optical paths.

The OCT light source unit 1001, like a general Swept Source type OCT apparatus, is configured to include a wavelength scanning type (wavelength sweep type) light source which can scan (sweep) the wavelength of emission light. The OCT light source unit 1001 temporally varies the output wavelength in a near-infrared wavelength which is not visually recognizable by the eyes of a human. Light emitted from the OCT light source unit 1001 is indicated by sign L0.

The light L0, which is output from the OCT light source unit 1001, is guided to a polarization controller 1003 by an optical fiber 1002, and the polarization state of the light L0 is adjusted. The polarization controller 1003 adjusts the polarization state of the light L0 that is guided through the optical fiber 1002, by applying stress from outside to the optical fiber 1002 which is formed, for example, in a loop shape.

The light L0, the polarization state of which was adjusted by the polarization controller 1003, is guided to a fiber coupler 1005 by an optical fiber 1004, and is divided into the measurement light LS and reference light LR.

As illustrated in FIG. 14, the reference light LR is guided to a collimator 1007 by an optical fiber 1006 and converted to a parallel beam. The reference light LR, which is converted to the parallel beam, travels through an optical path length correction member 1008 and a dispersion compensation member 1009, and is guided to a corner cube 1010. The optical path length correction member 1008 functions as delay means for making coincident the optical lengths (optical distances) of the reference light LR and measurement light LS. The dispersion compensation member 1009 functions as dispersion compensation means for making coincident the dispersion characteristics of the reference light LR and measurement light LS.

The corner cube 1010 changes the direction of travel of the reference light LR, which is converted to the parallel beam by the collimator 1007, to an opposite direction. The optical path of the reference light LR, which is incident on the corner cube 1010, and the optical path of the reference light LR, which is emitted from the corner cube 1010, are parallel. In addition, the corner cube 1010 is configured to be movable in a direction along the incidence optical path and emission optical path of the reference light LR. By this movement, the length of the optical path (reference optical path) of the reference light LR is changed.

As illustrated in FIG. 14, the reference light LR, which has traveled via the corner cube 1010, travels through the dispersion compensation member 1009 and optical path length correction member 1008, is converted from the parallel beam to a convergent beam by a collimator 1011, made incident on an optical fiber 1012 and guided to a polarization controller 1013, and the polarization state of the reference light LR is adjusted.

The polarization controller 1013 has, for example, the same configuration as the polarization controller 1003. The reference light LR, the polarization state of which was adjusted by the polarization controller 1013, is guided to an attenuator 1015 by an optical fiber 1014, and the light amount is adjusted under the control of an arithmetic control unit 12. The reference light LR, the light amount of which was adjusted by the attenuator 1015, is guided to a fiber coupler 1017 by an optical fiber 1016.

The measurement light LS generated by the fiber coupler 1005 is guided to the collimate lens 502 by an optical fiber 501. As referred to in FIG. 10(A) and FIG. 10(B), the measurement light made incident on the collimate lens 502 is radiated on the subject eye 81 via the galvano mirrors 503a and 503b, first optical member 510, first reflecting member 511, second optical member 512, second reflecting member 513, and OCT measurement optical system objective lens 507. The measurement light is reflected/scattered at various depth positions of the subject eye 81. Backscattered light of the measurement light by the subject eye 81 travels through the same path as the forward path in an opposite direction, and, as illustrated in FIG. 14, is guided to the fiber coupler 1005 and arrives at the fiber coupler 1017 via an optical fiber 1018.

The fiber coupler 1017 generates interference light by compounding (causing interference between) the measurement light LS made incident via the optical fiber 1018 and the reference light (LR) made incident via the optical fiber 1016. The fiber coupler 1017 generates a pair of interference lights LC by branching the interference light of the measurement light LS and reference light LR at a predetermined branching ratio (e.g. 50:50). The pair of interference lights LC emitted from the fiber coupler 1017 are guided to a detector 1021 by two optical fibers 1019 and 1020, respectively.

The detector 1021 is, for example, a balanced photodiode (Balanced Photo Diode: hereinafter "BPD") which includes a pair of photodetectors which detect a pair of interference lights LC, respectively, and outputs a difference between detection results by the photodetectors. The detector 1021 sends a detection result (detection signal) to the arithmetic control unit 12. The arithmetic control unit 12 forms a tomographic image by applying a Fourier transform or the like to a spectrum distribution based on the detection result obtained by the detector 1021, for example, with respect to each of serial wavelength scans (with respect to each A line). The arithmetic control unit 12 causes a display unit 13 to display the formed image.

In the present embodiment, although a Michelson interferometer is adopted, an interferometer of a freely chosen type, for example, a Mach-Zehnder interferometer, may be applied.

4. Shape of Objective Lens

Figure 15:
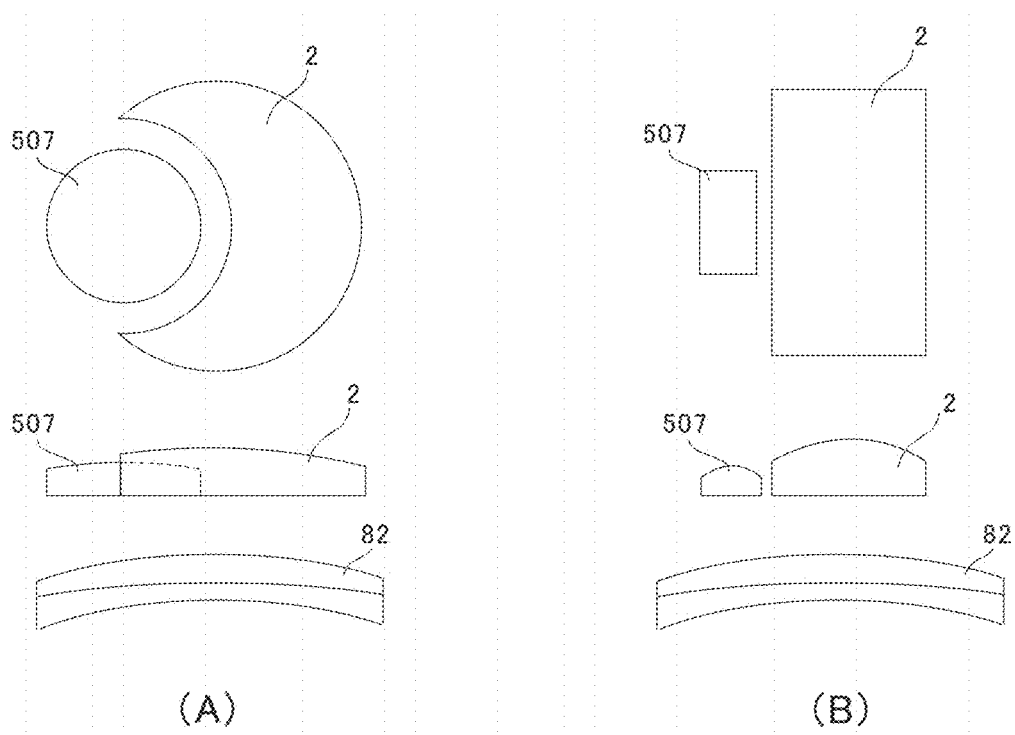
FIG. 15 is an explanatory view illustrating design modes of the objective lens of the present invention.
Figure 16:
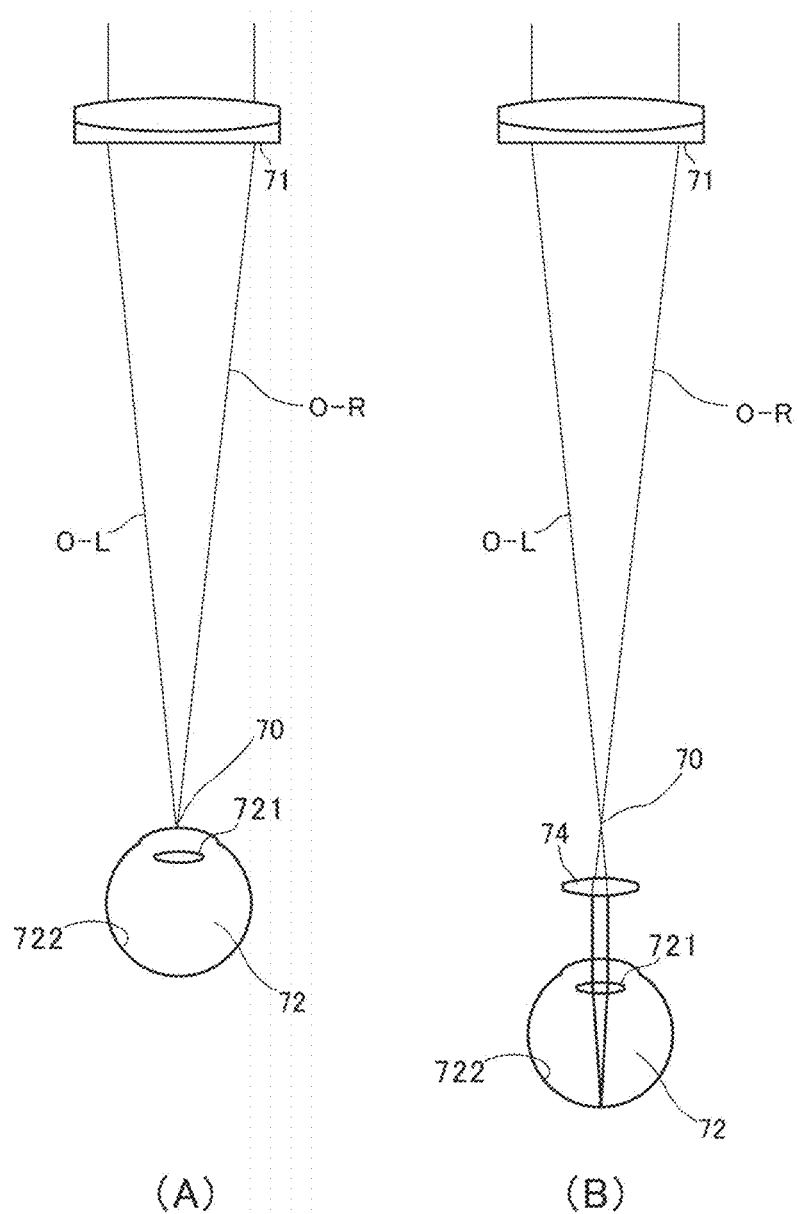
FIG. 16(A) is a view illustrating an observation optical system at a time of observing an anterior ocular segment by an ophthalmic microscope.
FIG. 16(B) is a view illustrating an observation optical system at a time of observing a posterior ocular segment by an ophthalmic microscope.
Figure 17:
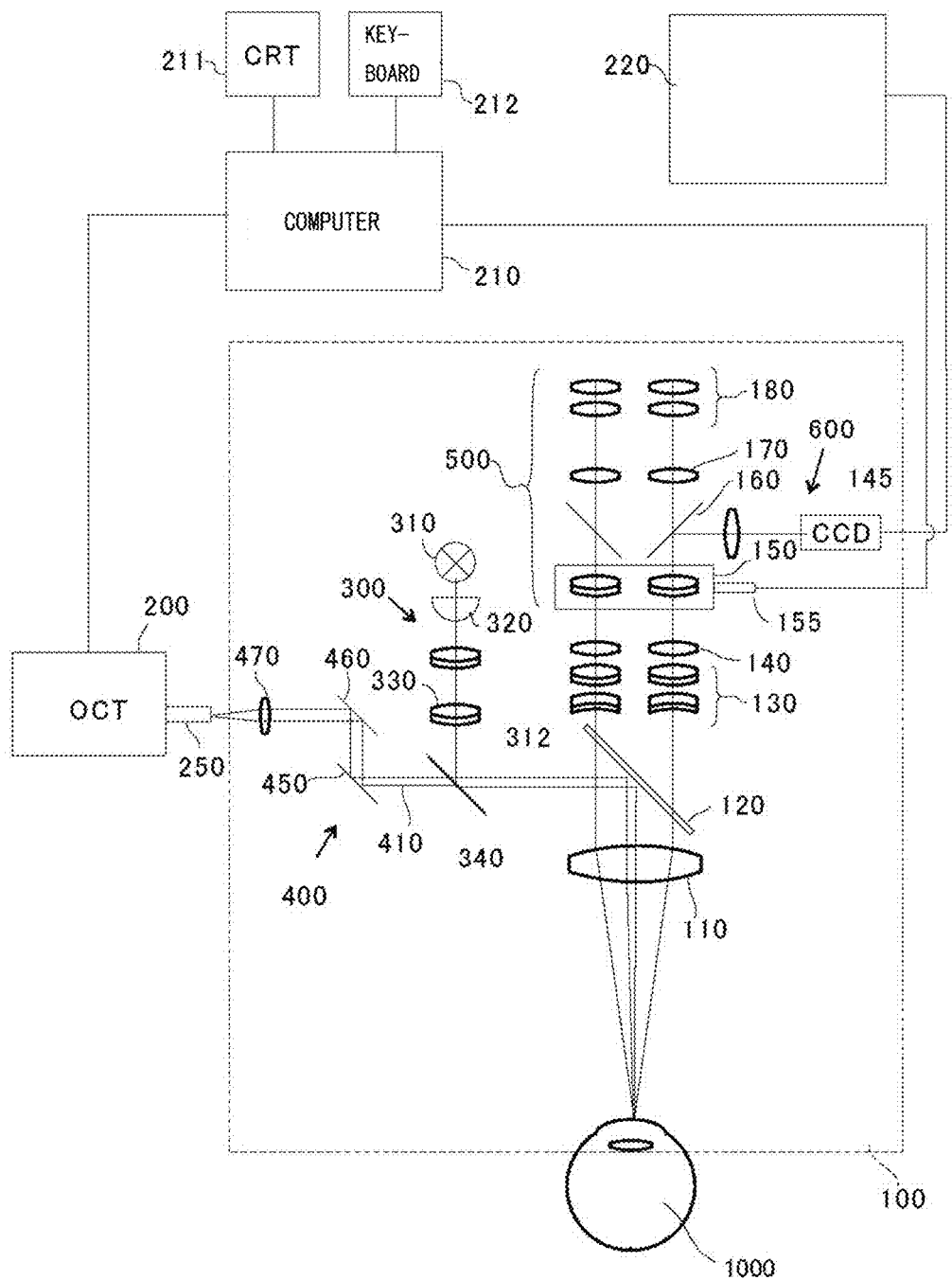
FIG. 17 is an explanatory view of prior art of an ophthalmic microscope equipped with an OCT function.

FIG. 15 is an explanatory view illustrating other concrete examples of the objective lens 2 for the observation optical system and the OCT measurement optical system objective lens 507. FIG. 15(A) is a view illustrating an objective lens 2 for the observation optical system, which is configured such that a circular convex lens is cut by a curved surface (a partial circle in plan-view shape) which is parallel to the optical axis, and a circular OCT measurement optical system objective lens 507 (convex lens) which is disposed in the cut part. FIG. 15(B) is a view illustrating an objective lens 2 for the observation optical system with a rectangular shape in plan view, which is configured such that a circular convex lens is cut by a plane parallel to the optical axis, and an OCT measurement optical system objective lens 507 (convex lens) with a rectangular shape in plan view, which is disposed in the cut part.

The embodiments of the present invention have been described above. The present invention is not limited to the above embodiments, and changes of conditions, etc., which are made without departing from the spirit of the invention, are all within the scope of the present invention.

REFERENCE SIGNS LIST

Reference signs used in FIG. 1 to FIG. 15 denote the following.

1 Ophthalmic microscope
2 Objective lens
5 OCT apparatus
6 Ophthalmic microscope main body
7 OCT function expansion unit
9 Illumination light source
10 OCT unit
12 Arithmetic control unit
13 Display unit
14 Front lens
81 Subject eye
82 Objective auxiliary lens
300 Illumination optical system
301 Optical fiber
302 Emission light diaphragm
303 Condenser lens
304 Illumination field diaphragm
305 Collimate lens
306 Reflection mirror
400 Observation optical system
400L Left-eye observation optical system
400R Right-eye observation optical system
401 Variable power lens system
402 Beam splitter
403 Imaging lens
404 Image erecting prism
405 Interpupillary distance adjusting prism
406 View field diaphragm
407 Ocular lens
500 OCT measurement optical system
501 Optical fiber
502 Collimate lens
503 Scanning function unit
503a Galvano mirror
503b Galvano mirror
507 OCT measurement optical system objective lens
510 First optical member
511 First reflecting member
512 Second optical member
513 Second reflecting member
1001 OCT light source unit
1002 Optical fiber
1003 Polarization controller
1004 Optical fiber
1005 Fiber coupler
1006 Optical fiber
1007 Collimator
1008 Optical path length correction member
1009 Dispersion compensation member
1010 Corner cube
1011 Collimator
1012 Optical fiber
1013 Polarization controller
1014 Optical fiber
1015 Attenuator
1016 Optical fiber
1017 Fiber coupler
1018 Optical fiber
1019 Optical fiber
1020 Optical fiber 1021 Detector
1100 Photographing optical system
1101 Imaging lens
1102 Reflection mirror
1103 TV camera
L0 Light
LC Interference light
LR Reference light
LS Measurement light
O-300 Optical axis of illumination optical system
O-400 Optical axis of observation optical system
O-400L Optical axis of left-eye observation optical system
O-400R Optical axis of right-eye observation optical system
O-500 Optical axis of OCT measurement optical system
O-501 First optical axis
O-502 Second optical axis
O-503 Third optical axis
U1 First focal point
U2 Second focal point
U3 Third focal point

The invention claimed is:

1. An ophthalmic microscope with a function of switchably performing anterior ocular segment observation and posterior ocular segment observation with respect to a subject eye, comprising:
an observation optical system having a first focal point in front of the subject eye;
an objective auxiliary lens configured to be capable of being set in a position on the subject eye side of an objective lens in the observation optical system or on a side opposite to the subject eye side, or capable of being released from the position, a focal point at a time when the objective auxiliary lens is set being set to a second focal point which is an anterior ocular segment position of the subject eye;
a front lens configured to be capable of being set in a position further toward the subject eye side than the first focal point or being released from the position, a focal point through a crystalline lens of the subject eye at a time when the front lens is set being set to a third focal point which is a posterior ocular segment position of the subject eye, and
an OCT measurement optical system, the OCT measurement optical system including an OCT measurement optical system objective lens,
wherein the objective auxiliary lens is set and the front lens is released during the anterior ocular segment observation, without changing a positional relationship between the objective lens and the subject eye,
wherein the front lens is set and the objective auxiliary lens is released during the posterior ocular segment observation, without changing the positional relationship between the objective lens and the subject eye,
wherein the observation optical system includes the objective lens having such a shaped that a part of a circular lens is cut off,
wherein the OCT measurement optical system includes the OCT measurement optical system objective lens which is disposed in the cut-off part of the objective lens, has a first focal point in front of the subject eye, and is configured such that an optical path of OCT measurement light passes through the objective auxiliary lens,
wherein when the objective auxiliary lens is set and the front lens is released, a focal point is set to a second focal point which is an anterior ocular segment position of the subject eye, and OCT measurement of the anterior ocular segment is performed, and
wherein when the front lens is set and the objective auxiliary lens is released, a focal point is set to a third focal point which is a posterior ocular segment position of the subject eye, and OCT measurement of the posterior ocular segment is performed.

2. The ophthalmic microscope according to claim 1, wherein
the OCT measurement optical system further includes:
a first optical member configured to guide light from an OCT light source in a first optical axis direction;
a first reflecting member configured to guide the light guided in the first optical axis direction in a second optical axis direction substantially orthogonal to the first optical axis direction;
a second optical member configured to relay the light guided in the second optical axis direction; and
a second reflecting member configured to guide the light relayed by the second optical member in a third optical axis direction substantially orthogonal to the second optical axis direction, and
the OCT measurement optical system objective lens is disposed on the third optical axis direction and radiates the light guided in the third optical axis direction onto a predetermined portion of the subject eye.

3. The ophthalmic microscope according to claim 1, further comprising a mechanism configured such that the front lens is released when the objective auxiliary lens is set, and the objective auxiliary lens is released when the front lens is set.

4. The ophthalmic microscope according to claim 1, wherein the objective auxiliary lens is a concave lens.

5. The ophthalmic microscope according to claim 1, wherein the ophthalmic microscope includes a plurality of kinds of the front lenses, and a plurality of kinds of the objective auxiliary lenses corresponding to the front lenses.

6. An OCT function expansion unit configured to add an OCT measurement optical system to an ophthalmic microscope main body which includes a front lens capable of being set on or released from an optical path of an observation optical system, thereby being capable of effecting switching between anterior ocular segment observation and posterior ocular segment observation with respect to a subject eye, the OCT function expansion unit comprising:
a replacement objective lens for replacement of an objective lens of the observation optical system of the microscope main body,
wherein
the replacement objective lens has such a shape that a part of a circular lens is cut off,
an OCT measurement optical system objective lens is provided in the cut-off part of the replacement objective lens,
the observation optical system, in which the objective lens is replaced with the replacement objective lens, and the OCT measurement optical system have a first focal point in front of the subject eye,
an objective auxiliary lens is provided which is configured to be capable of being set in a position located further toward the subject eye side than the replacement objective lens and the OCT measurement optical system objective lens or located on an opposite side to the subject eye, or capable of being released from the position, a focal point at a time when the objective auxiliary lens is set being set to a second focal point which is an anterior ocular segment position of the subject eye, when the front lens is set in a position further toward the subject eye side than the first focal point, a focal point through a crystalline lens of the subject eye is set to a third focal point which is a posterior ocular segment position of the subject eye, the objective auxiliary lens is set and the front lens is released during the anterior ocular segment observation, and the front lens is set and the objective auxiliary lens is released during the posterior ocular segment observation, whereby switching between the anterior ocular segment observation and the posterior ocular segment observation by the observation optical system and the OCT measurement optical system is enabled without changing a positional relationship between the objective lens and the subject eye.

7. The OCT function expansion unit according to claim 6, wherein the OCT measurement optical system includes:
a first optical member configured to guide light from an OCT light source in a first optical axis direction;
a first reflecting member configured to guide the light guided in the first optical axis direction in a second optical axis direction substantially orthogonal to the first optical axis direction;
a second optical member configured to relay the light guided in the second optical axis direction; and
a second reflecting member configured to guide the light relayed by the second optical member in a third optical axis direction substantially orthogonal to the second optical axis direction, and the OCT measurement optical system objective lens is disposed on the third optical axis direction and radiates the light guided in the third optical axis direction onto a predetermined portion of the subject eye.

* * * * *